US012150975B2

(12) United States Patent
Niesor et al.

(10) Patent No.: US 12,150,975 B2
(45) Date of Patent: Nov. 26, 2024

(54) THERAPEUTIC COMBINATIONS TO TREAT RED BLOOD CELL DISORDERS

(71) Applicant: HARTIS-PHARMA SA, Nyon (CH)

(72) Inventors: Joseph Eric Niesor, Nyon (CH); Renee Benghozi, Charenton le Pont (FR); Francois Lamour, Blotzheim (FR)

(73) Assignee: HARTIS-PHARMA SA, Nyon (CH)

( * ) Notice: Subject to any disclaimer, the term of this patent is extended or adjusted under 35 U.S.C. 154(b) by 693 days.

(21) Appl. No.: 16/320,647

(22) PCT Filed: Jul. 26, 2017

(86) PCT No.: PCT/EP2017/068938
§ 371 (c)(1),
(2) Date: Jan. 25, 2019

(87) PCT Pub. No.: WO2018/019911
PCT Pub. Date: Feb. 1, 2018

(65) Prior Publication Data
US 2019/0167767 A1 Jun. 6, 2019

(30) Foreign Application Priority Data

Jul. 27, 2016 (EP) .................................... 16181521
Oct. 28, 2016 (EP) .................................... 16196326

(51) Int. Cl.
| | | |
|---|---|---|
| *A61K 38/45* | (2006.01) |
| *A61K 31/045* | (2006.01) |
| *A61K 31/05* | (2006.01) |
| *A61K 31/07* | (2006.01) |
| *A61K 31/122* | (2006.01) |
| *A61K 31/167* | (2006.01) |
| *A61K 31/192* | (2006.01) |
| *A61K 31/216* | (2006.01) |
| *A61K 31/355* | (2006.01) |
| *A61K 31/421* | (2006.01) |
| *A61K 31/4439* | (2006.01) |
| *A61K 31/455* | (2006.01) |
| *A61K 31/517* | (2006.01) |
| *A61K 31/724* | (2006.01) |
| *A61K 38/17* | (2006.01) |
| *A61K 45/06* | (2006.01) |
| *A61P 3/06* | (2006.01) |

(52) U.S. Cl.
CPC ............ *A61K 38/45* (2013.01); *A61K 31/045* (2013.01); *A61K 31/05* (2013.01); *A61K 31/07* (2013.01); *A61K 31/122* (2013.01); *A61K 31/167* (2013.01); *A61K 31/192* (2013.01); *A61K 31/216* (2013.01); *A61K 31/355* (2013.01); *A61K 31/421* (2013.01); *A61K 31/4439* (2013.01); *A61K 31/455* (2013.01); *A61K 31/517* (2013.01); *A61K 31/724* (2013.01); *A61K 38/17* (2013.01); *A61K 38/1709* (2013.01); *A61K 45/06* (2013.01); *A61P 3/06* (2018.01); *C12Y 203/01043* (2013.01)

(58) Field of Classification Search
CPC ...... A61K 38/45; A61K 31/045; A61K 31/05; A61K 31/07; A61K 31/122; A61K 31/167; A61K 31/192; A61K 31/216; A61K 31/355; A61K 31/421; A61K 31/4439; A61K 31/455; A61K 31/517; A61K 31/724; A61K 38/17; A61K 38/1709; A61K 45/06; A61P 3/06; C12Y 203/01043
See application file for complete search history.

(56) References Cited

U.S. PATENT DOCUMENTS

| | | |
|---|---|---|
| 4,643,988 A | 2/1987 | Segrest et al. |
| 6,004,925 A | 12/1999 | Dasseux et al. |
| 6,218,436 B1 | 4/2001 | Howard et al. |
| 6,287,590 B1 | 9/2001 | Dasseux |
| 6,316,503 B1 | 11/2001 | Li et al. |
| 6,426,365 B1 | 7/2002 | Shinkai et al. |
| 6,582,721 B1 | 6/2003 | Lang |
| 6,602,854 B1 | 8/2003 | Dasseux et al. |
| 6,663,900 B2 | 12/2003 | DeFreitas et al. |
| 6,664,230 B1 | 12/2003 | Fogelman et al. |

(Continued)

FOREIGN PATENT DOCUMENTS

| | | |
|---|---|---|
| WO | WO 98/35937 | 8/1998 |
| WO | WO 2004/020393 | 3/2004 |

(Continued)

OTHER PUBLICATIONS

Pubchem, "Linoleic acid". National Center for Biotechnology Information (2022). PubChem Compound Summary for CID 5280450, Linoleic acid <URL: https://pubchem.ncbi.nlm.nih.gov/compound/Linoleic-acid#section=Chemical-and-Physical-Properties> (Year: 2022).*

(Continued)

*Primary Examiner* — Robert J Yamasaki
*Assistant Examiner* — Trevor Kane
(74) *Attorney, Agent, or Firm* — SALIWANCHIK, LLOYD & EISENSCHENK

(57) ABSTRACT

The present invention is related to a combination useful in the prevention and/or treatment of red blood cell disorders, in particular, acute and chronic complications associated with red blood cell dysfunction, increased red blood cell cholesterol and decreased plasma levels of lipophilic antioxidant (sickle cell disease, thalassemia, diabetes). The invention in particular relates to pharmaceutical formulations, regimens, methods of treatment and uses thereof.

14 Claims, 2 Drawing Sheets

(56) References Cited

U.S. PATENT DOCUMENTS

| | | | |
|---|---|---|---|
| 6,743,778 | B2 | 6/2004 | Kohno |
| 6,753,313 | B1 | 6/2004 | Dasseux et al. |
| 6,930,085 | B2 | 8/2005 | Fogelman et al. |
| 6,933,279 | B2 | 8/2005 | Fogelman et al. |
| 7,307,058 | B2 | 12/2007 | Dasseux et al. |
| 7,332,514 | B2 | 2/2008 | Maeda et al. |
| 7,439,323 | B2 | 10/2008 | Bielicki |
| 7,579,504 | B2 | 8/2009 | Koltun et al. |
| 8,114,995 | B2 | 2/2012 | Hansen et al. |
| 8,148,323 | B2 | 4/2012 | Remaley et al. |
| 8,242,144 | B2 | 8/2012 | Wong et al. |
| 8,394,808 | B2 | 3/2013 | Pinto et al. |
| 8,436,152 | B2 | 5/2013 | Brinkman et al. |
| 8,541,236 | B2 | 9/2013 | Heinecke et al. |
| 8,568,766 | B2 | 10/2013 | Anantharamaiah et al. |
| 8,703,783 | B2 | 4/2014 | Zheng et al. |
| 8,748,394 | B2 | 6/2014 | Murase et al. |
| 8,765,186 | B2 | 7/2014 | Schäfer et al. |
| 8,835,378 | B2 | 9/2014 | Remaley et al. |
| 8,912,237 | B2 | 12/2014 | Voelker |
| 8,936,787 | B2 | 1/2015 | Remaley et al. |
| 8,993,628 | B2 | 3/2015 | Forman et al. |
| 8,999,920 | B2 | 4/2015 | Wright et al. |
| 9,000,022 | B2 | 4/2015 | Busch et al. |
| 9,125,943 | B2 | 9/2015 | Vucica et al. |
| 9,173,890 | B2 | 11/2015 | Murase et al. |
| 9,187,551 | B2 | 11/2015 | Dasseux et al. |
| 9,416,135 | B2 | 8/2016 | Dong et al. |
| 9,422,363 | B2 | 8/2016 | Anantharamaiah et al. |
| 9,439,946 | B2 | 9/2016 | Wright et al. |
| 2004/0053842 | A1* | 3/2004 | Nguyen .................. A61P 11/00 514/313 |
| 2007/0191377 | A1* | 8/2007 | Worcel .................. A61K 31/502 514/471 |
| 2008/0096900 | A1 | 4/2008 | Kayser et al. |
| 2008/0119571 | A1* | 5/2008 | Khanna .................... A61P 3/06 435/11 |
| 2014/0023631 | A1 | 1/2014 | Auerbach et al. |

FOREIGN PATENT DOCUMENTS

| | | | |
|---|---|---|---|
| WO | WO 2010/144904 | 12/2010 | |
| WO | WO 2014/015318 | 1/2014 | |
| WO | WO-2014015318 A1 * | 1/2014 | ......... A61K 48/0083 |
| WO | WO 2015/195491 | 12/2015 | |
| WO | WO 2016/071907 | 5/2016 | |

OTHER PUBLICATIONS

DifferenceBetween, "Difference Between Linoleic Acid and Conjugated Linoleic Acid" DifferenceBetween.com, Biology, Sep. 9, 2015 <URL: https://www.differencebetween.com/difference-between-linoleic-acid-and-vs-conjugated-linoleic-acid/> (Year: 2015).*

Gammone, "Carotenoids: potential allies of cardiovascular health?". Food Nutr Res. 2015; 59: 10.3402/fnr.v59.26762 <URL: https://www.ncbi.nlm.nih.gov/pmc/articles/PMC4321000/> (Year: 2015).*

Ruiz-Núñez, Begoña, et al. "Supplementation of patients with sickle cell disease with astaxanthin increases plasma-and erythrocyte-astaxanthin and may improve the hemolytic component of the disease." Free Radicals and Antioxidants 3 (2013): S22-S29. (Year: 2013).*

Niesor, Eric J., and Renée Benghozi. "Potential signal transduction regulation by HDL of the β2-adrenergic receptor pathway. implications in selected pathological situations." Archives of Medical Research 46.5 (2015): 361-371. (Year: 2015).*

Yanpanitch, Orn-uma, et al. "Treatment of β-thalassemia/hemoglobin E with antioxidant cocktails results in decreased oxidative stress, increased hemoglobin concentration, and improvement of the hypercoagulable state." Oxidative medicine and cellular longevity 2015 (2015). (Year: 2015).*

Boretti, Alberto. "Curcumin-Based Fixed Dose Combination Products for Cholesterol Management: A Narrative Review." ACS Pharmacology & Translational Science (2024). (Year: 2024).*

Packer, Lester. "Interactions among antioxidants in health and disease: vitamin E and its redox cycle." Proceedings of the Society for Experimental Biology and Medicine 200.2 (1992): 271-276. (Year: 1992).*

Acton, S. et al. "Identification of Scavenger Receptor SR-BI as a High Density Lipoprotein Receptor" *Science*, Jan. 26, 1996, pp. 518-520, vol. 271.

Akinyanju, P. A. et al. "Plasma and Red Cell Lipids in Sickle Cell Disease" *Annals of Clinical and Laboratory Science*, 1976, pp. 521-524, vol. 6, No. 6.

Alassane, D. et al. "Serum lipids and oxidized low density lipoprotein levels in sickle cell disease: Assessment and pathobiological significance" *African Journal of Biochemistry Research*, Feb. 2014, pp. 39-42, vol. 8, No. 2.

Ama Moor, V. J. et al. "Oxidative profile of sickle cell patients in a Cameroonian urban hospital" *BMC Clinical Pathology*, 2016, pp. 1-5, vol. 16.

Amer, J. et al. "Flow cytometric measurement of reactive oxygen species production by normal and thalassaemic red blood cells" *European Journal of Haematology*, 2003, pp. 84-90, vol. 70.

Barnes, H. J. "Blood Rheology in Diabetes Mellitus" *Acta Medica Portuguesa*, 1986, S36-S39, vol. 7.

Buchko, G. W. et al. "Structural Studies of a Peptide Activator of Human Lecithin-Cholesterol Acyltransferase" *The Journal of Biological Chemistry*, Feb. 9, 1996, pp. 3039-3045, vol. 271, No. 6.

Buchwald, H. et al. "Brief Review Effect of Plasma Cholesterol on Red Blood Cell Oxygen Transport" *Clinical and Experimental Pharmacology and Physiology*, 2000, pp. 951-955, vol. 27.

Buchwald, H. et al. "Plasma Cholesterol: An Influencing Factor in Red Blood Cell Oxygen Release and Cellular Oxygen Availability" *J Am Coll Surg*, Nov. 2000, pp. 490-497, vol. 191, No. 5.

Bruckert, E. et al. "The replacement of arginine by cysteine at residue 151 in Apolipoprotein A-I produces a phenotype similar to that of Apolipoprotein A-I$_{Milano}$" *Atherosclerosis*, 1997, pp. 121-128, vol. 128.

Chinetti, G. et al. "PPAR-α and PPAR-γ activators induce cholesterol removal from human macrophage foam cells through stimulation of the ABCA1 pathway" *Nature Medicine*, Jan. 2001, pp. 53-58, vol. 7, No. 1.

Coisne, C. et al. "β-Cyclodextrins Decrease Cholesterol Release and ABC-Associated Transporter Expression in Smooth Muscle Cells and Aortic Endothelial Cells" *Frontiers in Physiology*, May 2016, pp. 1-14, vol. 7, Article 185.

Cooper, R. A. et al. "The Role of Membrane Lipids in the Survival of Red Cells in Hereditary Spherocytosis" *The Journal of Clinical Investigation*, 1969, pp. 736-744, vol. 48.

Cooper, R. A. et al. "The Selective and Conjoint Loss of Red Cell Lipids" *The Journal of Clinical Investigation*, 1969, pp. 906-914, vol. 48.

Costet, P. et al. "Sterol-dependent Transactivation of the ABC1 Promoter by the Liver X Receptor/Retinoid X Receptor" *The Journal of Biological Chemistry*, Sep. 8, 2000, p. 28240-28245, vol. 275, No. 36.

Da Silva, D. G. H. et al. "Impact of genetic polymorphisms in key enzymes of homocysteine metabolism on the pathophysiology of sickle cell anemia" *Free Radical Biology and Medicine*, 2017, pp. 53-61, No. 106.

Emokpae, M. A. et al. "Lecithin: Cholesterol acyltransferase, lipoprotein lipase and lipoproteins in adult Nigerians with sickle cell disease" *African Journal of Biochemistry Research*, Feb. 2010, pp. 17-20, vol. 4, No. 2.

Fabry, M. E. "Transgenic animal models of sickle cell disease" *Experienfia*, 1993, pp. 28-36, vol. 49.

Franceschini, G. et al. "A-I$_{Milano}$ Apoprotein Decreased High Density Lipoprotein Cholesterol Levels With Significant Lipoprotein Modifications and Without Clinical Atherosclerosis in an Italian Family" *J. Clin. Invest.*, Nov. 1980, pp. 892-900, vol. 66.

Freeman, L. A. et al. "Lecithin:Cholesterol Acyltransferase Activation by Sulfhydryl-Reactive Small Molecules: Role of Cysteine-31" *The Journal of Pharmacology and Experimental Therapeutics*, Aug. 2017, pp. 306-318, vol. 362.

Gunawardane, R. N. et al. "Agonistic Human Antibodies Binding to Lecithin-Cholesterol Acyltransferase Modulate High Density Lipo-

(56) References Cited

OTHER PUBLICATIONS protein Metabolism" *The Journal of Biological Chemistry*, Feb. 5, 2016, pp. 2799-2811, vol. 291, No. 6.

Hamdy, M. M. et al. "Selenium and Vitamin E as antioxidants in chronic hemolytic anemia: Are they deficient? A case-control study in a group of Egyptian children" *Journal of Advanced Research*, 2015, pp. 1071-1077, vol. 6.

Hermann, P. B. et al. "Erythrocyte oxidative stress markers in children with sickle cell disease" *Jornal de Pediatria*, 2016, pp. 1-6.

Homan, R. et al. "A Fluorescence Method to Detect and Quantitate Sterol Esterification by Lecithin: Cholesterol Acyltransferase" *Anal Biochem.*, Oct. 1, 2013, pp. 1-18, vol. 441, No. 1.

Hung, K. T. et al. "Red Blood Cells Play a Role in Reverse Cholesterol Transport" *Arterioscler Thromb Vasc Biol.*, Jun. 2012, pp. 1-12, vol. 32, No. 6.

Jain, S. K. et al. "Red Blood Cell [$^{14}$C]Cholesterol Exchange and Plasma Cholesterol Esterifying Activity of Normal and Sickle Cell Blood" *Biochimica et Biophysica Acta*, 1982, pp. 11-15, No. 688.

Kato, G. J. et al. "Deconstructing sickle cell disease: Reappraisal of the role of hemolysis in the development of clinical subphenotypes" *Blood Rev.* Jan. 2007, pp. 1-16, vol. 21, No. 1.

Kilsdonk, E. P. C. et al. "Cellular Cholesterol Efflux Mediated by Cyclodextrins" *The Journal of Biological Chemistry*, Jul. 21, 1995, pp. 17250-17256, vol. 270, No. 29.

Krieger, M. et al. "Molecular Flypaper, Host Defense, and Atherosclerosis" *The Journal of Biological Chemistry*, Mar. 5, 1993, pp. 4569-4572, vol. 268, No. 7.

Lamers, C. et al. "Therapeutic modulators of peroxisome proliferator-activated receptors (PPAR): a patent review (2008-present)" *Journal Expert Opinion on Therapeutic Patents*, 2012, pp. 803-841, vol. 22, No. 7.

Motoyama, K. et al. "Involvement of Lipid Rafts of Rabbit Red Blood Cells in Morphological Changes Induced by Methylated β-Cyclodextrins" *Biol. Pharm. Bull.*, Apr. 2009, pp. 700-705, vol. 32, No. 4.

Muskiet, F. A. J. et al. "Supplementation of patients with homozygous sickle cell disease with zinc, α-tocopherol, vitamin C, soybean oil, and fish oil$^{1-3}$" *The American Journal of Clinical Nutrition*, 1991, pp. 736-744, vol. 54.

Namazi, G. et al. "Association of the Total Cholesterol Content of Erythrocyte Membranes with the Severity of Disease in Stable Coronary Artery Disease" *Cholesterol*, 2014, pp. 1-6, vol. 2014.

Natta, C. et al. "Low serum levels of carotenoids in sickle cell anemia" *Eur J Haematol.*, 1988, pp. 131-135, vol. 41.

Nayak, B. S. et al. "Determination of RBC membrane and serum lipid composition in trinidadian type II diabetics with and without nephropathy" *Vascular Health and Risk Management*, 2008, pp. 893-899, vol. 4, No. 4.

Niesor, E. J. et al. "Modulating cholesteryl ester transfer protein activity maintains efficient pre-β-HDL formation and increases reverse cholesterol transport" *Journal of Lipid Research*, 2010, pp. 3443-3454, vol. 51.

Ou, J. et al. "L-4F, an Apolipoprotein A-1 Mimetic, Dramatically Improves Vasodilation in Hypercholesterolemia and Sickle Cell Disease" *Circulation*, May 13, 2003, pp. 2337-2341.

Ozturk, O. H. et al. "Lipoprotein Subfraction Profile and HDL-Associated Enzymes in Sickle Cell Disease Patients" *Lipids*, 2013, pp. 1217-1226, vol. 48.

Picaud, S. et al. "RVX-208, an inhibitor of BET transcriptional regulators with selectivity for the second bromodomain" *PNAS*, Dec. 3, 2013, p. 19754-19759, vol. 110, No. 49.

Ryan, T. M. et al. "Knockout-Transgenic Mouse Model of Sickle Cell Disease" *Science*, Oct. 31, 1997, pp. 873-876, vol. 278.

Sandor, B. et al. "Effects of Poloxamer 188 on red blood cell membrane properties in sickle cell anaemia" *British Journal of Haematology*, 2016, pp. 145-149, vol. 173.

Seixas, M. O. et al. "Levels of high-density lipoprotein cholesterol (HDL-C) among children with steady-state sickle cell disease" *Lipids in Health and Disease*, 2010, pp. 1-9, vol. 9, No. 91.

Semple, G. et al. "1-Alkyl-benzotriazole-5-carboxylic Acids Are Highly Selective Agonists of the Human Orphan G-Protein-Coupled Receptor GPR109b" *J. Med. Chem.*, 2006, pp. 1227-1230, vol. 49.

Sethi, A. A. et al. "Asymmetry in the Lipid Affinity of Bihelical Amphipathic Peptides A Structural Determinant for the Specificity of ABCA1-Dependent Cholesterol Efflux By Peptides" *The Journal of Biological Chemistry*, Nov. 21, 2008, pp. 32273-32282, vol. 283, No. 47.

Shamburek, R. D. et al. "Familial Lecithin:Cholesterol Acyltransferase Deficiency: First-in-Human Treatment with Enzyme Replacement" *J Clin Lipidol.*, 2016, pp. 1-27, vol. 10, No. 2.

Shinkai, H. "Cholesteryl ester transfer protein inhibitors as high-density lipoprotein raising agents" *Journal Expert Opinion on Therapeutic Patents*, 2009, pp. 1229-1237, vol. 19. No. 9.

Simon, D. I. et al. "Atherothrombosis: Seeing Red?" *Circulation*, Nov. 17, 2015, pp. 1-5, vol. 132, No. 20.

Soudijn, W. et al. "Nicotinic Acid Receptor Subtypes and Their Ligands" *Medicinal Research Reviews*, 2007, pp. 417-433, vol. 27, No. 3.

Stamos, T. D. et al. "Low high density lipoprotein levels are associated with an elevated blood viscosity" *Atherosclerosis*, 1999, pp. 161-165, vol. 146.

Tangney, C. C. et al. "Selected Indices of Micronutrient Status in Adult Patients With Sickle Cell Anemia (SCA)" *American Journal of Hematology*, 1989, pp. 161-166, vol. 32.

Uehara, Y. et al. "FAMP, a Novel ApoA-I Mimetic Peptide, Suppresses Aortic Plaque Formation Through Promotion of Biological HDL Function in ApoE-Deficient Mice" *J Am Heart Assoc.*, 2013, pp. 1-15.

Uehara, Y. et al. "High-Density Lipoprotein-Targeted Therapy and Apolipoprotein A-I Mimetic Peptides" *Circulation Journal*, Dec. 2015, pp. 2523-2528, vol. 79.

Unchern, S. et al. "Oxidative Modification and Poor Protective Activity of HDL on LDL Oxidation in Thalassemia" *Lipids*, 2010, pp. 627-633, vol. 45.

Vaisman, B. L. et al. "Measurement of Lecithin-Cholesterol Acyltransferase Activity with the Use of a Peptide-Proteoliposome Substrate" *Methods Mol Biol.*, 2013, pp. 343-352, vol. 1027.

Vichinsky, E. "Emerging 'A' therapies in hemoglobinopathies: agonists, antagonists, antioxidants, and arginine" *Hematology*, 2012, pp. 271-275.

Voskou, S. et al. "Oxidative stress in β-thalassaemia and sickle cell disease" *Redox Biology*, 2015, pp. 226-239, vol. 6.

Watson, C. E. et al. "Treatment of patients with cardiovascular disease with L-4F, an apo-A1 mimetic, did not improve select biomarkers of HDL function" *Journal of Lipid Research*, 2011, pp. 361-373, vol. 52.

Westerman, M. P. et al. "Erythrocyte and Plasma Lipids in Sickle Cell Anemia" *Blood*, Feb. 1964, pp. 200-205, vol. 23. No. 2.

Wood, K. C. et al. "Sickle cell disease vasculopathy: A state of nitric oxide resistance" *Free Radical Biology & Medicine*, 2008, pp. 1506-1528, vol. 44.

Written Opinion in International Application No. PCT/EP2017/068938, Sep. 27, 2017, pp. 1-8.

Yang, C.-J. et al. "Fukuoka University apolipoprotein A-I mimetic peptide (FAMP): A novel potential therapeutic for myocardial ischemia reperfusion injury" *International Journal of Cardiology*, 2016, pp. 1059-1060, vol. 222.

Yuditskaya, S. et al. "Proteomic identification of altered apolipoprotein patterns in pulmonary hypertension and vasculopathy of sickle cell disease" *Blood*, Jan. 2009, pp. 1122-1128, vol. 113, No. 5.

Zannos-Mariolea, L. et al. "Serum Vitamin E Levels with Beta-Thalassaemia Major: Preliminary Report" *British Journal of Haematology*, 1974, pp. 193-199, vol. 26.

Zhu, X. et al. "Cysteine mutants of human apolipoprotein A-I: a study of secondary structural and functional properties" *Journal of Lipid Research*, 2005, pp. 1303-1311, vol. 46.

Zorca, S. et al. "Lipid Levels in Sickle-Cell Disease Associated With Hemolytic Severity, Vascular Dysfunction and Pulmonary Hypertension" *Br J Haematol.*, May 2010, pp. 1-17, vol. 149, No. 3.

(56) References Cited

OTHER PUBLICATIONS

Boudrahem-Addour, N. et al. "Oxidative Status and Plasma Lipid Profile in β-Thalassemia Patients" *Hemoglobin*, 2014, pp. 1-6.
Renoux, C. et al. "Effect of Age on Blood Rheology in Sickle Cell Anaemia and Sickle Cell Haemoglobin C Disease: A Cross-Sectional Study" *Plos One*, Jun. 29, 2016, pp. 1-11.
Niesor, E. J. et al. "Red Blood Cell Membrane Cholesterol May Be a Key Regulator of Sickle Cell Disease Microvascular Complications" *Membranes*, Nov. 11, 2022, pp. 1-15, vol. 12, No. 1134.

* cited by examiner

THERAPEUTIC COMBINATIONS TO TREAT RED BLOOD CELL DISORDERS

CROSS-REFERENCE TO RELATED APPLICATION

This application is the U.S. national stage application of International Patent Application No. PCT/EP2017/068938, filed Jul. 26, 2017.

FIELD OF THE INVENTION

The present invention relates to a combined formulation or use in the prevention and/or treatment of red blood cell disorders, in particular, acute and chronic complications associated with red blood cell dysfunction, increased red blood cell cholesterol and decreased plasma levels of lipophilic antioxidant (sickle cell disease, thalassemia, diabetes).

BACKGROUND OF THE INVENTION

Sickle Cell Anemia (SCA) is the common manifestation of Sickle Cell Disease (SCD) and most frequent hemoglobinopathy in the world, affecting over 50 million people worldwide. SCA significantly impairs quality of life and shortens lifespan. While hemolytic anemia and frequent vaso-occlusive crises are the most frequent complications for patients suffering from SCA, these patients are also at very high risk for developing pulmonary hypertension, cerebral vasculopathy leading to stroke, osteonecrosis, retinopathy, priapism, leg ulcers, acute chest syndrome and glomerulopathy (Kato et al., 2007, *Blood Rev*, 21(1), 37-47). Sickle Red Blood Cells (RBCs) are very rigid and fragile. The loss of RBC deformability is considered to be the primary factor responsible for the vaso-occlusive events, severe hemolytic anemia and progressive organ damages in patients suffering from above mentioned diseases. It should also be noted that a high concentration of cholesterol in RBC decreases its capacity to transport oxygen (Buchwald et al., 2000, *J Am Coll Surg*, 91(5), 490-7; Buchwald et al., 2000, *Clin Exp Pharmacol Physiol*, 27(12): p. 951-5), thus detrimental to and triggering the sickling process. It is estimated that 5% of the world population is affected by these hemoglobinopathies for which very few treatments are available. In addition to SCD and Thalassemia, low HDL levels, high RBC membrane cholesterol, high blood viscosity (Stamos and Rosenson, 1999, *Atherosclerosis*, 146(1), 161-5) and low blood levels of lipophilic antioxidant, are also observed in more common pathologies of the general population such as diabetes (Barnes, 1986, *Acta Med Port.* 7(5-6), S36-9) and cardiovascular diseases (Namazi et al., 2014, *Cholesterol, article ID*:821686; Simon and Silverstein, 2015, *Circulation*, 132(20), 1860-2) and may be at the origin of diabetes complications.

Attempts to address simultaneously the common features linking these disregulations affecting SCD, thalassemia and diabetes have not been made and vascular as well as microvascular complications of these diseases are still unmet medical needs.

Several studies reported decreased high-density lipoprotein-cholesterol (HDL-C) level in SCD (Seixas et al., 2010, *Lipids Health Dis*, 9, 91) which may lead to an increased risk for endothelial dysfunction for patients suffering from this disease (Yuditskaya et al., 2009, *Blood*, 113(5), 1122-1128). This association could be related to the release of oxidized fatty acids during lipolysis (Sandor et al., 2016, *Br J Haematol*, 173(1), 145-9), leading to endothelial cell inflammation (Yuditskaya et al., 2009, supra).

Although sharing common mechanisms with atherosclerosis (oxidative stress, inflammation and vascular adhesion), SCA vasculopathy clearly differs in that cholesterol accumulation in arterial wall and atheroma have not been reported (Zorca et al., 2010, *Br J Haematol*, 149(3), 436-45). Intriguingly, while plasma total lipids and cholesterols levels are usually lower in SCA than in healthy individuals, the level of total lipids and cholesterol is higher in the RBC membrane of SCA patients compared to controls (Westerman et al., 1964, *Blood*, 23, 200-5) which could be related to the decreased plasma Lecithin Cholesterol Acyl Transferase (LCAT) level found in SCD patients (Jain, et al. 1982, *Biochim Biophys Acta.*, 688:11-15. and Emokpae, et al. 2010, *Afr J Biochem Res.*, 4:17-20) and more particularly during vaso-occlusive crises (Homan et al., 2013, *Anal Biochem*, 441(1), 80-6).

Patients with Sickle Cell Disease and Thalassemia have repeatedly been observed to display low HDL-C and low LDL-C plasma levels but increased oxidized LDL and plasma levels for the markers of oxidation (Voskou et al., 2015, *Redox Biology*, 6, 226-239, Boudrahem-Addour et al., 2015, *Hemoglobin*, 39(1):36-41; Unchern et al., 2010, *Lipids*, 45:627-633). The role of HDL in removing cholesterol from peripheral tissues such as macrophages is well established, in contrast to its potential role in removing excess cholesterol from RBC which has been and is still poorly investigated and thus offers very restricted therapeutic perspectives. As early as 1976, RBC from SCD patients were observed to be significantly enriched in cholesterol as compared to heathy control subjects (Akinyanju et. al., 1976, *Ann Clin Lab Sci.*, 6(6):521-4).

L-4F, an ApoA1 mimetic (U.S. Pat. No. 6,664,230) was shown to improve vasodilation in hypercholesterolemia and in an animal model of Sickle Cell Disease (Ou et al 2003, *Circulation*, 107(18): 2337-41) but not in human clinical studies. Indeed, L-4F treatment, delivered by either subcutaneous injection or intravenous infusion to patients with cardiovascular disease, did not improve HDL functional biomarkers despite achieving plasma levels that improved identical biomarkers ex vivo and in animal models (Watson, et al., 2011, 52: 361-373).

Sickle cell disease, thalassemia, and glucose-6-phosphate-dehydrogenase deficiency are all hereditary disorders with higher potential for oxidative damage due to chronic redox imbalance in red cells that often results in clinical manifestation of mild to severe hemolysis in patients with these disorders. Hamdy et al., (2015, *Journal of Advanced Research*, 6, 1071-1077), found a decreased antioxidant level in both SCD and thalassemia and considered accelerated oxidative damage as one of the hallmarks in both SCD and thalassemia. More importantly, Tangney et al. (1989, *Am J Hematol*, 32(3), 161-6) observed that although dietary analyses suggest that dietary intakes of SCA individuals exceeded the recommended daily allowances of all macro- and micronutrients measured (specifically, beta carotene, alpha carotene, and cryptoxanthin), all serum values for carotenoids examined, specifically, beta carotene, alpha carotene, and cryptoxanthin were markedly depressed when compared to those of healthy controls. These results suggest that in individuals with SCA, several micronutrients vital for maintaining the antioxidative capacities are present in lower quantities in plasma/serum.

In addition, Natta et al., 1988, *Eur J Haematol*, 41(2), 131-5 measured a decrease of major carotenoids, beta carotene, cryptoxanthin, lycopene, lutein, as well as alpha-tocopherol and retinol in plasma of SCA patients.

Vitamin E levels in plasma have been consistently found to be decreased in patients suffering from thalassemia. For example, Zannos-Mariolea et al., 1974, *Br J Haematol,* 26(2), 193-9 reported that serum vitamin E level was below normal (<0.5 mg/100 ml) in 46% of the 56 children with major beta-thalassaemia (P<0.001) evaluated in their study.

The low level of plasma lipophilic antioxidant in SCD and thalassemia may enhance the pathological manifestations of increased oxidative stress well established in these diseases.

It is important to note that attempts to provide vitamin E as dietary supplement alone have not been successful for treating SCD pathologies (Muskiet et al., 1991, *Am J Clin Nutr,* 54(4): p. 736-44).

From a review of therapeutic approaches to treat the oxidative status of SCD, vitamin E and other lipophilic antioxidant alone have not been considered as effective therapeutic treatment of SCD (Vichinsky, 2012, *Hematology Am Soc Hematol Educ Program,* 271-5).

SCD is a disease that worsens over time and no treatment is available. The use of hydroxyurea is the only currently approved disease modifying treatments for people affected with SCD. Hydroxyurea is used in primary and secondary stroke prevention. Although it has not been shown to prevent all SCD-related organ damage, the treatment modalities can improve the quality of life for individuals suffering from SCD. Stem cell transplants from bone marrow or blood of healthy donors are also used for treating Sickle Cell Anemia. Complications from hydroxyurea therapy and stem cell transplants are rare but can be serious or life-threatening. Thalassemia syndrome can be a life-threatening hemolytic anemia requiring chronic blood transfusion and removal of excess iron. Managing patients with transfusion-dependent β-thalassemia major still remains a challenge for clinicians and despite an effective transfusion protocol, transfusion hemosiderosis is a primary cause of mortality in these patients.

Thus, there is an urgent need for finding new treatment approaches for those life threatening disorders.

SUMMARY OF THE INVENTION

The present invention relates to a new combination for use as a therapy for treating acute and chronic complications associated with red blood cell dysfunction, increased red blood cell cholesterol and decreased plasma levels of lipophilic antioxidant (sickle cell disease, thalassemia, diabetes). The present invention is based on the unexpected discovery that the combination of the induction of an increase of the HDL activity together with a dietary supplement, parenteral, subcutaneous or intra venous administration (as a free or fixed combination) of liposoluble antioxidants acts synergistically for treating the rheological complications of the red blood cell disorders, in particular increased red blood cell cholesterol found in sickle cell disease as well as thalassemia and subsequently will contribute to treating and/or preventing microvascular damages and associated pathologies (retinopathies, kidney failure, leg ulcer, priapism, acute chest syndrome, stroke) such as those found in SCD or thalassemia. Further, the combination according to the invention can advantageously act on red blood cells' volume, hydration, shape or rheological properties by rendering them closer to parameters found for healthy patients.

According to one aspect, the invention provides a combination of at least one agent increasing HDL activity and at least one liposoluble antioxidant or a mixture thereof for use in the prevention and/or treatment of a disease or disorder characterized by acute and chronic complications associated with red blood cell dysfunction, increased red blood cell cholesterol and decreased plasma levels of lipophilic antioxidant, in particular for the prevention and/or treatment of acute and chronic complications associated with red blood cell dysfunction in sickle cell disease, thalassemia and diabetes.

According to another aspect, the invention provides the use of a combination of at least one agent increasing HDL activity and at least one liposoluble antioxidant or a mixture thereof for the preparation of a pharmaceutical formulation useful in the prevention and/or treatment of a disease or disorder characterized by acute and chronic complications associated with red blood cell dysfunction, increased red blood cell cholesterol and decreased plasma levels of lipophilic antioxidant, in particular for the prevention and/or treatment of acute and chronic complications associated with red blood cell dysfunction in sickle cell disease, thalassemia and diabetes.

According to another aspect, the invention provides a pharmaceutical composition comprising of at least one agent increasing HDL activity and at least one liposoluble antioxidant or a mixture thereof and a pharmaceutically acceptable carrier, diluent or excipient thereof.

According to another aspect, the invention provides an agent increasing HDL activity for use in the prevention and/or treatment of a disease or disorder characterized by acute and chronic complications associated with red blood cell dysfunction, increased red blood cell cholesterol and decreased plasma levels of lipophilic antioxidant, in particular for the prevention and/or treatment of acute and chronic complications associated with red blood cell dysfunction in sickle cell disease, thalassemia and diabetes, wherein said compound is to be administered in combination with at least one liposoluble antioxidant or a mixture thereof.

According to another aspect, the invention provides a method of preventing and/or treating a disease or disorder characterized by acute and chronic complications associated with red blood cell dysfunction in sickle cell disease, thalassemia and diabetes, said method comprising administering at least one agent increasing HDL activity in combination with at least one liposoluble antioxidant or a mixture thereof to a subject in need thereof.

DETAILED DESCRIPTION

Figure 1:
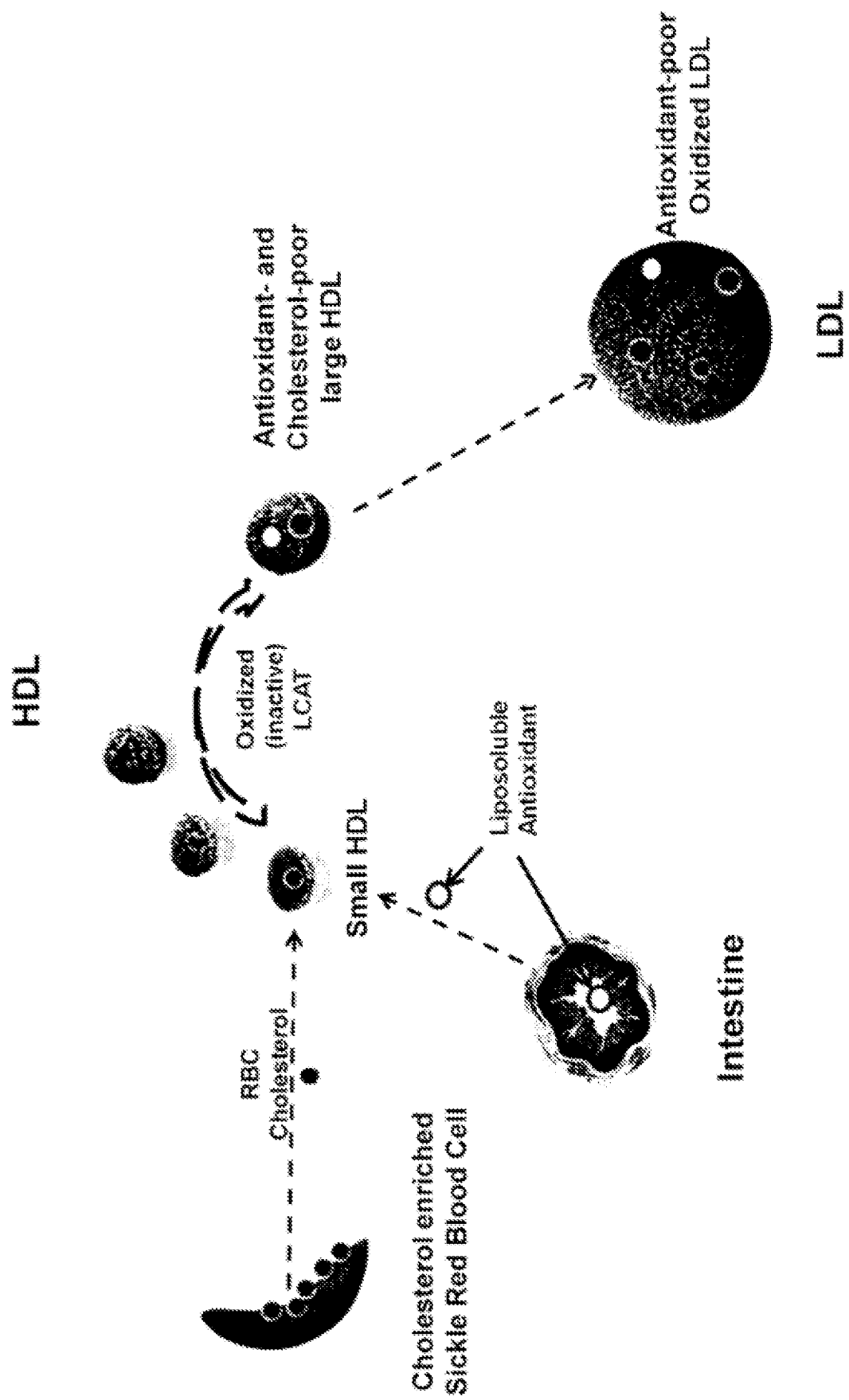
FIG. 1 is a schematic representation of the low HDL cholesterol, LCAT activity, liposoluble antioxidant and high RBC cholesterol and oxidized LDL in non treated SCD, where Sickle cell disease red blood cells are enriched in cholesterol and display pathological rheological properties leading to vascular and microvascular complications. Oxidized inactive Lecithin Cholesterol Acyl Transferase (LCAT) cannot generate efficiently large cholesterol rich HDL. Liposoluble antioxidant are not efficiently absorbed through the intestine and distributed to LDL, resulting in oxidized and highly atherogenic LDL.
Figure 2:
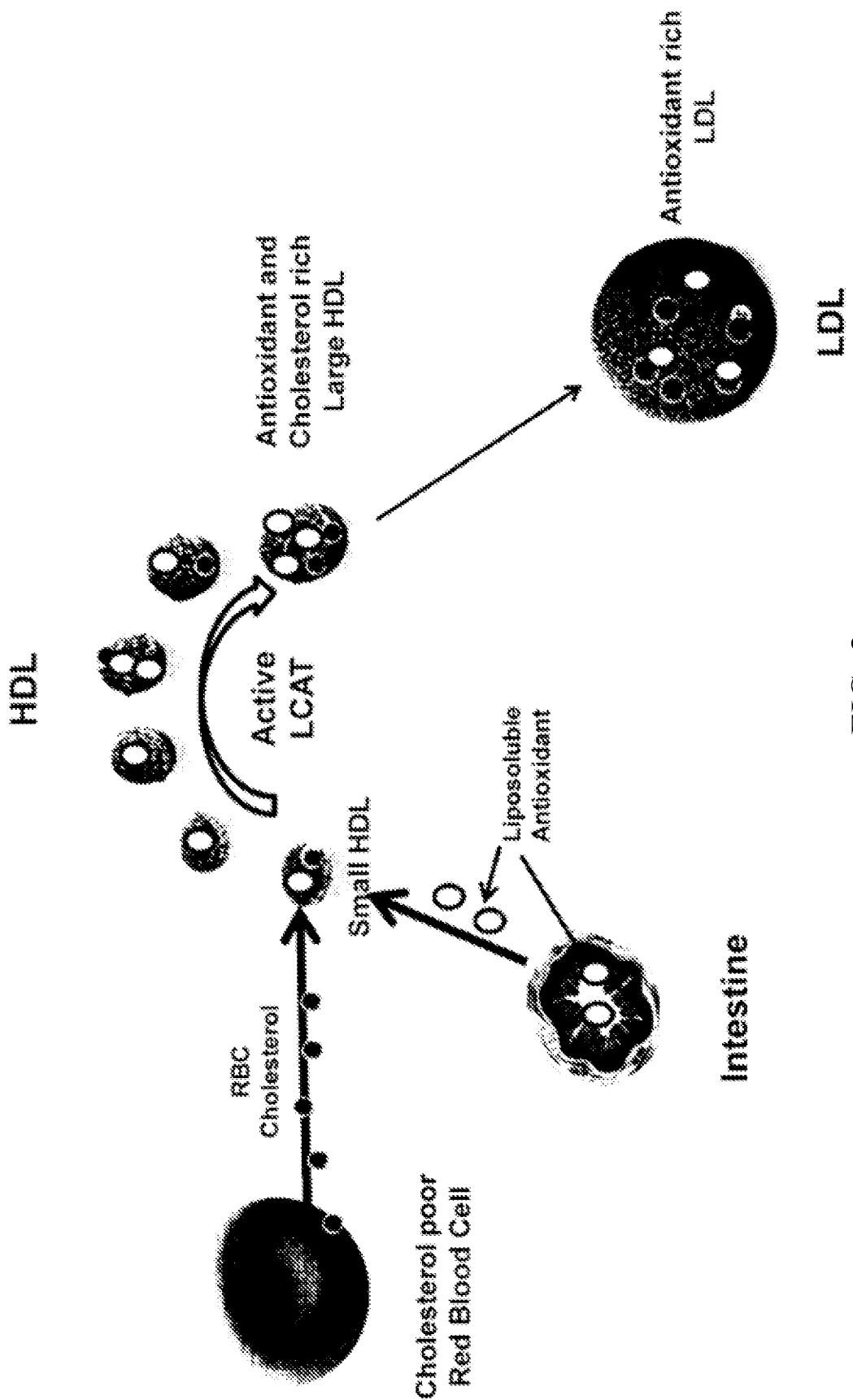
FIG. 2 is a schematic representation of High HDL cholesterol, LCAT activity, liposoluble antioxidant and low RBC cholesterol in SCD subjects treated with a combination or a method according to the invention, wherein combined administration of least one agent increasing HDL activity and at least one liposoluble antioxidant or a mixture thereof leads to an increase in active HDL, thereby leading to efficient removal of cholesterol from sickle cell disease red blood cells and restores their normal rheological properties diminishing macro- and micro-vascular complications. In addition, liposoluble antioxidants supplements are more efficiently absorbed through the intestine via the HDL pathway and then distributed to LDL, resulting in less atherogenic LDL. In a less oxidative milieu Lecithin Cholesterol Acyl Transferase (LCAT) activity produces more efficiently the atheroprotective large cholesterol rich HDL.

Plasma HDL is formed through the interaction between Apolipoprotein A1 (ApoA1) and ATP-binding cassette transporter (ABCA1) the later effluxing numerous lipophilic molecules (such as cholesterol, phospholipids, plant sterols, vitamin E, lutein and zeaxanthin) to ApoA1 thus forming a nascent HDL particle (discoidal pre-betal-HDL particle). LCAT activity will further increase the capacity of HDL to take-up and transport more of the above lipophilic molecules. This cargo will be delivered to the HDL receptor (scavenger receptor class B type I, SRB-1) expressing cells (Monty-Krieger et al., 1993, *Journal Biological Chemistry* 268: 4568-4572) and/or exchanged with several tissues including the circulating RBC which are in close vicinity of the plasma HDL pool.

ApoA1 displays the unique capacity of removing cholesterol from loaded cell membranes through a membrane transporter action (ABCA1 and ABCG1) or by diffusion following the concentration gradient. The phenomenon called reverse cholesterol transport whereby peripheral cellular cholesterol is transferred to HDL for delivery to the liver, has been very well documented using cholesterol labelled-macrophages. It is to be noted that the larger plasma pool of RBC cholesterol that has been shown to play an important role in this process (Hung et al., 2012, *Arterioscler Thromb Vasc Biol.*, 32(6): 1460-1465) has not been thoroughly investigated.

Therefore, for improving the regulation of RBC cholesterol levels, agents capable of enhancing the HDL activity can be selected from HDL enhancers, HDL peptide mimetics or HDL analogues.

Therapeutic approaches targeting HDL have been reviewed recently by Uehara et al., 2015, *Circ J,* 79(12), 2523-8. In particular, LCAT activators, CETP inhibitors and modulators, ApoA1 mimetics, full-length ApoA1, ApoA1-mimetic peptides such as 5A, D-4F, L-4F, FAMP such as described in Uehara et al., 2015, *Circ J,* 79(12), 2523-8 and analogues, reconstituted HDL, including ApoA1-phospholipid complexes, ApoA1 Milano, ApoE phospholipid complexes are considered as HDL enhancers.

The term "HDL enhancer" refers to agents that are able to increase the plasma level of HDL/ApoA1, agents capable of enhancing ApoA1 production or plasma accumulation or increasing the ApoA1 turnover. Examples of those enhancers comprise hormone receptor activators which have been shown to increase ApoA1 production such as PPAR agonists as reviewed by Lamers et al, 2012, *Journal Expert Opinion on Therapeutic Patents,* 22(7), 802-841, in particular PPAR alpha agonists. For example, enhancing HDL formation has been achieved by increasing ApoA1 production by tissues such as liver and intestine with PPAR alpha agonists (fibrates), Thyroid Receptor agonists and Niacin and analogues. Therefore, those agents can be used as agents capable of enhancing HDL activity according to the invention. Alternatively, plasma HDL can be raised by increasing ABCA1 activity through activation of the Liver X Receptor (LXR) a direct regulator of ABCA1 gene expression, for example by using activators of the Liver X Receptor (LXR) such as TO901317 (U.S. Pat. No. 6,316,503). Further, Human recombinant LCAT protein can be infused into animal and human to HDL enhancers according to the invention to increase plasma HDL lipids and apolipoproteins. Similarly, agents increasing plasma LCAT level (Shamburek et al 2016, *Journal of Clinical Lipidology,* 10, 356-367), enhancing LCAT activity (Gunawardane et al., 2016, *J Biol Chem,* 291(6), 2799-811) and modified LCAT protein with enhanced enzymatic activity which are under development increase plasma HDL can be used as HDL enhancers in the context of the invention.

The term "HDL (peptide) mimetic" refers to agents mimicking the properties of ApoA1 in the formation of HDL particles through binding to ABCA1 and in increasing efflux of cholesterol, phospholipids and other lipophilic substances. A large number of peptides mimicking multiple repeats of 22 amino acids (22-mer) from human ApoA1 being able to form amphipathic a helices have been synthetized and display some of the properties of ApoA1 and especially with regard to their ability to remove cell membrane cholesterol. For instance, HDL peptide mimetic include 5A, D-4F and L-4F, all ApoA1 mimetics. FAMP differs from other ApoA1 mimetics because it is designed to specifically interact with human ABCA1 without engaging the nonspecific, passive efflux pathway. Therefore, it functions similarly to human ApoA1. Furthermore, FAMP markedly increases pre-β HDL particles (nascent HDL particles) as well as overall cholesterol efflux from peripheral tissues. Therefore, ApoA1 mimetics, full-length ApoA1, ApoA1-mimetic peptides such as D-4F, L-4F, FAMP and analogues may be used as agents capable of enhancing the HDL activity according to the invention. According to another particular aspect, peptide 5A and analogues thereof as described in Sethi et al., 2008, *J Biol Chem.,* 283 (47): 32273-32282, U.S. Pat. Nos. 8,148,323; 8,835,378; 8,936, 787 can be used as agents capable of enhancing the HDL activity according to the invention.

The term "HDL analogue" refers to any particle containing at least one HDL-like particle associated with an apolipoprotein (ApoA1, ApoA2, ApoE, ApoC1, ApoC3, ApoL, ApoM, ApoAIV etc.) alone or prepared as a lipoprotein complex. Reconstituted HDL (U.S. Pat. No. 9,125,943), including ApoA1-phospholipid complexes such as ApoA1 Milano (Franceshini et al, 1980, *J. Clin. Investig.,* 66, 892-900) or ApoA1 Paris (Bruckert et al., 1997, *Atherosclerosis,* 128, 121-128), ApoE-phospholipid complexes can be in particular used as agents capable of enhancing the HDL activity according to the invention.

The term "ApoA1 mimetics" refers to substances, in particular peptides that mimics the properties of ApoA1, in particular in its ability to mobilize cellular or lipoprotein lipids and transport and deliver said lipids to cells and tissues. ApoA1 mimetics comprise ApoA1 analogues, in particular but limited to those as specifically defined herein, i.e. peptides or peptidomimetics having a sequence analogous to the ApoA1 sequence. Further, the term "ApoA1 mimetics" refers also to non-peptidic substances such as a cyclodextrin or cyclodextrine derivatives, that mimics the properties of ApoA1, in particular in its ability to mobilize cellular or lipoprotein lipids and transport and deliver said lipids to cells and tissues (Kilsdonk et al., 1995, *J Biol Chem.,* 270(29):17250-6; Coisne at al., 2016, *Front Physiol.,* 7:185). Examples of cyclodextrins or cyclodextrine derivatives include, but are not limited to beta-cyclodextrins such as sulfobutylether-beta-cyclodextrin, 2-hydroxypropyl-beta-cyclodextrin, methyl-beta-cyclodextrin and 2,6-di-Omethylbeta-cyclodextrin. The preferred cyclodextrins are sulfobutylether-beta-cyclodextrin and 2-hydroxypropyl-beta-cyclodextrin.

The term an "ApoA1 inducer" refers to inducers of the ApoA1 gene expression such as Nuclear Hormone Receptor Agonists. Examples of ApoA1 inducers comprise, but are not limited to, LXR (Liver X Receptor), RXR (retinoid X receptor), ROR (RAR-related orphan receptors), PPAR agonists. The ability of an agent to act as an ApoA1 inducer can be assayed by standard methods such as described in Chinetti et al., 2001, Nat Med. 7(1):53-8.

The term a "Lecithin Cholesterol Acyl Transferase (LCAT) activator" refers to an agent able to increase the level or enzymatic activity of LCAT. Examples of LCAT activators comprise, but are not limited to peptides such as LAP-20 (Buchko et al., 1996, J Biol Chem., 271(6): 3039-3045), but also comprise antibodies which bind to and activate LCAT such as those described in Gunawardane et al., 2016, J Biol Chem., 291(6):2799-811), and small molecules such as those described in Freeman et al., 2017, J Pharmacol Exp Ther., 362 (2), 306-318.

The ability of an agent to act as LCAT activator can be assayed by standard methods such as described in Vaisman et al., 2013 Methods Mol Biol., 1027:343-52 and Homan et al., 2013, Anal. Biochem., 441(1):80-6.

The term an "ATP Binding Cassette A1 (ABCA1) inducer" refers to an agent able to increase ABCA1 activity, for example through activation of the Liver X Receptor (LXR) a direct regulator of ABCA1 gene expression. The ability of an agent to act as ABCA1 inducer can be assayed by standard methods such as described in Costet et al., 2000, J Biol Chem. 275(36):28240-5. Examples of ABCA1 inducers comprise, but are not limited to activators of the LXR such as TO901317, and LXR activator such as those described in U.S. Pat. Nos. 6,316,503, 9,000,022, 7,579,504 or 8,993,628.

The term "niacin analogue" refers to compounds interacting with the Niacin receptor (Soudijn et al., 2007, Med Res Rev., 27(3):417-33). Examples of niacin analogues comprise, but are not limited to those described by Semple et al. 2006, J Med Chem., 49(4):1227-30.

The term "liposoluble vitamin" or "liposoluble antioxidant" refers to lipophilic agents having antioxidant properties such as tocopherols, tocotrienols and xanthophyll carotenoids.

The term "carotenoids" refers to one of the most widespread groups of pigments with more than 600 identified in nature. In plants, cyclization of lycopene either leads to the formation of beta-carotene or alpha-carotene and its derivative xanthophylls, beta-cryptoxanthin, zeaxanthin, astaxanthin, violaxanthin and lutein. Carotenes are characterized by cyclization at one or both ends whereas xanthophylls are formed by the introduction of oxygen. According to a particular aspect, carotenoids can be used as liposoluble vitamins according to the invention. In a further particular embodiment, carotenoids are selected from xanthophylls, lutein, zeaxanthin (e.g. meso-zeaxanthin), beta-cryptoxanthin, astaxanthin, and violaxanthin.

The terms "tocopherols" and "tocotrienols" refer to agents having vitamin E activity. There are eight naturally occurring vitamin E isoforms, alpha-, beta-, gamma- and delta-tocopherol and alpha-, beta-, gamma- and delta-tocotrienol. They are all potent liposoluble antioxidants, capable of neutralizing free radicals directly by donating hydrogen from its chromanol ring. Alpha-tocopherol is considered as the dominant form in vitamin E as the alpha-tocopherol transfer protein in the liver binds mainly alpha-tocopherol, thus preventing its degradation. According to a particular aspect, "tocopherols" and "tocotrienols" can be used as liposoluble vitamins according to the invention.

It is well recognized that hydrosoluble antioxidant such as vitamin C, glutathione, N-acetylcysteine and ions such as Zn etc. can regenerate liposoluble antioxidant and may be used to increase or maintain the antioxidant potential of liposoluble antioxidant.

As used herein, "treatment" and "treating" and the like generally mean obtaining a desired pharmacological and physiological effect. The effect may be prophylactic in terms of preventing or partially preventing a disease, symptom or condition thereof and/or may be therapeutic in terms of a partial or complete cure of a disease, condition, symptom or adverse effect attributed to the disease. The term "treatment" as used herein covers any treatment of a disease in a mammal, particularly a human, and includes: (a) preventing the disease from occurring in a subject which may be predisposed to the disease but has not yet been diagnosed as having it; (b) inhibiting the disease, i.e., arresting its development; or relieving the disease, i.e., causing regression of the disease and/or its symptoms or conditions.

According to a particular aspect, the efficacy of a treatment or a use according to the invention can be monitored through the decrease or abolition of acute and chronic complications associated with red blood cell dysfunction such as a decrease of red blood cell cholesterol or a sustained increase of plasma levels of lipophilic antioxidant by measuring the level of biomarkers of oxidative stress (for example antioxidants, oxidized lipids, Reactive Oxygen Species (ROS), malondialdehyde (MDA), glutathione, catalase etc.,) in total RBC and plasma. RBC rheological properties are also expected to be improved.

The term "subject" as used herein refers to mammals. For examples, mammals contemplated by the present invention include humans and the like.

Combinations of the Invention

According to a particular aspect, is provided a combination of at least one agent increasing HDL activity (e.g. HDL enhancing agent, HDL mimetic or HDL analogue) and at least one liposoluble antioxidant or a mixture thereof for use in the prevention and/or treatment of a disease or disorder characterized by acute and chronic complications associated with red blood cell dysfunction, increased red blood cell cholesterol and decreased plasma levels of lipophilic antioxidant.

Further, According to a particular aspect, is provided a combination of at least one agent increasing HDL activity is selected from an ApoA1 inducer, an HDL or ApoA1 mimetic or (mimicking compound), an ApoA1 and ApoE analogue, a Lecithin Cholesterol Acyl Transferase (LCAT) activator, a CETP inhibitor or modulator, a Peroxisome Proliferator Activated Receptor (PPAR) agonist and an ATP Binding Cassette A1 (ABCA1) inducer. According to a further particular embodiment, is provided a combination according to the invention wherein said at least one agent increasing HDL activity is selected from a recombinant Lecithin Cholesterol Acyl Transferase (LCAT) protein such as described in (US 2008/0096900 and US 2014/0023631 A1) (e.g. ACP-501, Shamburek et al. 2016, Journal of Clinical Lipidology, 10, 356-367).

According to another further particular embodiment, is provided a combination according to the invention wherein said at least one agent increasing HDL activity is a LCAT activator, for example such as peptide LAP-20 (Buchko et al., 1996, supra), or an antibody which binds to and activates LCAT.

According to another further particular embodiment, is provided a combination according to the invention wherein said at least one agent increasing HDL activity is selected from a wild type apolipoprotein A1 (ApoA1) (U.S. Pat. No. 8,436,152); mutant ApoA1 (U.S. Pat. No. 7,439,323) in particular such as ApoA1 Milano and ApoA1 Paris and ApoA1 mutants resistant to oxidation (U.S. Pat. No. 8,541, 236). Branched ApoA1 (U.S. Pat. No. 6,602,854) multimeric ApoA1 (U.S. Pat. Nos. 6,753,313; 7,307,058, 2), an ApoA1 analogue or an ApoA1 mimetic peptide (U.S. Pat. Nos. 4,643,988, 6,004,925; 8,748,394) such as L-4F. ApoA1 mimetic peptides orally bioavailable such as D-4F (U.S. Pat. Nos. 6,664,230; 6,933,279). Another class of ApoA1 mimetic peptides could be the Fukuoka University APOA-I Mimetic Peptides (FAMP) (Uehara Y. et al, 2013, *J Am Heart Assoc.;* 2(3):e000048. and Yang et al, 2016 *Int J Cardiol.,* 222:1059-60).

According to another further particular embodiment, is provided a combination according to the invention wherein said at least one agent increasing HDL activity is an agent mimicking ApoA1, such as for example selected peptides derived from ApoE (U.S. Pat. No. 9,422,363), from ApoA2 (U.S. Pat. No. 6,743,778), from ApoJ (U.S. Pat. Nos. 6,930, 085; 8,568,766) and any derived amphipathic helical peptide thereof, such as for example peptide 5A and analogues thereof (Sethi et al., supra; U.S. Pat. Nos. 8,148,323; 8,835, 378), such as those derived from ApoA1 and ApoA2 as well as from ApoC1, ApoC3, ApoJ, ApoL, ApoM, ApoAIV (U.S. Pat. No. 4,643,988). According to another further particular embodiment, is provided a combination according to the invention wherein said at least one agent increasing HDL activity is an HDL mimetic, such as a natural or synthetic ApoA1/phospholipid containing a wild type apolipoprotein A1 or a cysteine mutant (Zhu et al., 2005 *J. Lipid Res.,* 46:1303-131), including ApoA1 Milano (Franceshini et al, 1980, *J. Clin. Investig.,* 66, 892-900) or ApoA1 Paris (Bruckert et al., 1997, *Atherosclerosis*, 128, 121-128).

According to another further particular embodiment, is provided a combination according to the invention wherein said at least one agent increasing HDL activity is a natural or synthetic HDL particle analogue (e.g. an ApoA1/phospholipid mixture) such as CSL-111, CSL-112 (U.S. Pat. Nos. 9,125,943, 8,999,920 or 9,439,946) or CER-001 (U.S. Pat. Nos. 6,287,590 and 9,187,551).

According to another further particular embodiment, is provided a combination according to the invention wherein said at least one agent increasing HDL activity is a Peroxisome Proliferator-Activated Receptor (PPAR) activators (PPAR alpha, gamma or alpha-gamma co-activators) such as fenofibrate, pioglitazone or aleglitazar. According to another further particular embodiment, is provided a combination according to the invention wherein said at least one agent increasing HDL activity is including PPAR alpha/gamma co-agonists.

According to another further particular embodiment, is provided a combination according to the invention wherein said at least one agent increasing HDL activity is an agent enhancing ATP binding cassette A1 (ABCA1) expression such as a Liver X Receptor (LXR) modulator (U.S. Pat. No. 9,416,135) or LXR activator such as those described in U.S. Pat. Nos. 6,316,503, 9,000,022, 7,579,504 or 8,993,628.

According to another further particular embodiment, is provided a combination according to the invention wherein said at least one agent increasing HDL activity is a Bromodomain and Extra-Terminal (BET) protein inhibitor such as those described in U.S. Pat. No. 8,114,995, for example such as RVX-208 (Picaud et al., 2013, *PNAS,* 110, 49, 19755).

According to another further particular embodiment, is provided a combination according to the invention wherein said at least one agent increasing HDL activity is a Cholesteryl Ester Transfer Protein (CETP) inhibitor for example as reviewed by Shinkai et al, 2009, (*Expert Opin. Ther. Patents,* 19(9):1229-1237) such as anacetrapib and in particular a Cholesteryl Ester Transfer Protein (CETP) modulator such as those described in WO 2004/020393, WO 98/35937 and defined by Niesor et al., 2010, *JLR,* 51: 3443-3454 for example such as dalcetrapib.

According to another further particular embodiment, is provided a combination according to the invention wherein said at least one agent increasing HDL activity is an agent that upregulates the expression of ApoA1 (U.S. Pat. No. 8,242,144).

According to another further particular embodiment, is provided a combination according to the invention wherein said at least one agent increasing HDL activity or a mixture thereof is selected from Niacin and Niacin analogues which are compounds interacting with the Niacin receptor (Soudijn et al., 2007, supra), for example activators of the HM74 receptor, such as those described in U.S. Pat. Nos. 8,394,808 and 8,703,783 and niacin analogues as described by Semple et al. 2006, supra.

According to another further particular embodiment, is provided a combination according to the invention wherein said at least one liposoluble antioxidant or a mixture thereof is a xanthophyll such as lutein, zeaxanthin, meso-zeaxanthin, astaxanthin, beta-cryptoxanthin and combination thereof as described for example in U.S. Pat. Nos. 6,218, 436, 6,582,721 and 6,663,900.

According to another further particular embodiment, is provided a combination according to the invention wherein said at least one liposoluble antioxidant or a mixture thereof is a tocopherol isomer or derivative thereof such as alpha-, beta-, gamma- and delta-tocopherol.

According to another further particular embodiment, is provided a combination according to the invention wherein said at least one liposoluble antioxidant or a mixture thereof is a tocotrienol isomer or derivative thereof, such as alpha-, beta-, gamma- and delta-tocotrienol.

According to a particular aspect, the combination of the present invention is useful in the prevention and/or treatment of acute and chronic complications associated with red blood cell dysfunction, increased red blood cell cholesterol/decreased plasma levels of lipophilic antioxidant, such as those present in sickle cell disease, thalassemia or diabetes.

Pharmaceutical Compositions

According to another aspect, the invention provides a pharmaceutical composition comprising of at least one compound increasing HDL activity and at least one liposoluble antioxidant or a mixture thereof and a pharmaceutically acceptable carrier, diluent or excipient thereof.

Pharmaceutical compositions of the invention can contain one or more agent(s) of the invention in any form described herein. Compositions of this invention may further comprise one or more pharmaceutically acceptable additional ingredient(s), such as alum, stabilizers, antimicrobial agents, buffers, coloring agents, flavoring agents, adjuvants, and the like.

The agents of the invention, together with a conventionally employed adjuvant, carrier, diluent or excipient may be placed into the form of pharmaceutical compositions and unit dosages thereof, and in such form may be employed as solids, such as tablets or filled capsules, or liquids such as solutions, suspensions, emulsions, elixirs, or capsules filled with the same, all for oral use, or in the form of sterile injectable solutions for parenteral (including subcutaneous) use. Such pharmaceutical compositions and unit dosage forms thereof may comprise ingredients in conventional proportions, with or without additional active agents or principles, and such unit dosage forms may contain any suitable effective amount of the active ingredient commensurate with the intended dosage range to be employed. Compositions according to the invention are preferably oral.

Compositions of this invention may be liquid formulations, including, but not limited to, aqueous or oily suspensions, solutions, emulsions, syrups, and elixirs. Liquid forms suitable for oral administration may include a suitable aqueous or non-aqueous vehicle with buffers, suspending and dispensing agents, colorants, flavors and the like. The compositions may also be formulated as a dry product for reconstitution with water or other suitable vehicle before use. Such liquid preparations may contain additives, including, but not limited to, suspending agents, emulsifying agents, non-aqueous vehicles and preservatives. Suspending agents include, but are not limited to, sorbitol syrup, methyl cellulose, fructose, glucose/sugar syrup, gelatin, hydroxyethylcellulose, carboxymethyl cellulose, aluminum stearate gel, and hydrogenated edible fats. Emulsifying agents include, but are not limited to, lecithin, sorbitan monooleate, and acacia. Non-aqueous vehicles include, but are not limited to, edible oils, almond oil, fractionated coconut oil, oily esters, propylene glycol, and ethyl alcohol. Preservatives include, but are not limited to, methyl or propyl p-hydroxybenzoate and sorbic acid. Further materials as well as processing techniques and the like are set out in out in *Part 5 of Remington's "The Science and Practice of Pharmacy"*, 22$^{nd}$ Edition, 2012, *University of the Sciences in* Philadelphia, Lippincott Williams & Wilkins, which is incorporated herein by reference. Solid compositions of this invention may be in the form of tablets or lozenges formulated in a conventional manner. For example, tablets and capsules for oral administration may contain conventional excipients including, but not limited to, binding agents, fillers, lubricants, disintegrants and wetting agents. Binding agents include, but are not limited to, syrup, acacia, gelatin, sorbitol, tragacanth, mucilage of starch and polyvinylpyrrolidone. Fillers include, but are not limited to, lactose, sugar, microcrystalline cellulose, maizestarch, calcium phosphate, and sorbitol. Lubricants include, but are not limited to, magnesium stearate, stearic acid, talc, polyethylene glycol, and silica. Disintegrants include, but are not limited to, potato starch and sodium starch glycollate. Wetting agents include, but are not limited to, sodium lauryl sulfate. Tablets may be coated according to methods well known in the art.

Injectable compositions are typically based upon injectable sterile saline or phosphate-buffered saline or other injectable carriers known in the art.

Compositions of this invention may also be formulated as suppositories, which may contain suppository bases including, but not limited to, cocoa butter or glycerides. Compositions of this invention may also be formulated for inhalation, which may be in a form including, but not limited to, a solution, suspension, or emulsion that may be administered as a dry powder or in the form of an aerosol using a propellant, such as dichlorodifluoromethane or trichlorofluoromethane. Compositions of this invention may also be formulated transdermal formulations comprising aqueous or non-aqueous vehicles including, but not limited to, creams, ointments, lotions, pastes, medicated plaster, patch, or membrane.

Compositions of this invention may also be formulated for parenteral administration, including, but not limited to, by injection or continuous infusion. Formulations for injection may be in the form of suspensions, solutions, or emulsions in oily or aqueous vehicles, and may contain formulation agents including, but not limited to, suspending, stabilizing, and dispersing agents. The composition may also be provided in a powder form for reconstitution with a suitable vehicle including, but not limited to, sterile, pyrogen-free water.

Compositions of this invention may also be formulated as a depot preparation, which may be administered by implantation or by intramuscular injection. The compositions may be formulated with suitable polymeric or hydrophobic materials (as an emulsion in an acceptable oil, for example), ion exchange resins, or as sparingly soluble derivatives (as a sparingly soluble salt, for example).

Compositions of this invention may also be formulated as a liposome preparation. The liposome preparation can comprise liposomes which penetrate the cells of interest or the stratum corneum, and fuse with the cell membrane, resulting in delivery of the contents of the liposome into the cell. Other suitable formulations can employ niosomes. Niosomes are lipid vesicles similar to liposomes, with membranes consisting largely of non-ionic lipids, some forms of which are effective for transporting agents across the stratum corneum.

The agents of this invention can also be administered in sustained release forms or from sustained release drug delivery systems. A description of representative sustained release materials can also be found in the incorporated materials in Remington's Pharmaceutical Sciences. In addition ApoA1 analogues and mimetics can be formulated to produce a sustained release delivery system according to U.S. Pat. No. 9,173,890.

Various formulations of liposoluble antioxidant as described above can be used, in particular as described in U.S. Pat. No. 8,765,186 or 8,912,237.

Patients

In an embodiment, subjects according to the invention are subjects suffering from acute and chronic complications associated with red blood cell dysfunction such as increased red blood cell cholesterol Cooper and Jandl, 1969, *J Clin Invest.*, 48(4):736-44 and 48(5):906-14.; Akinyanju and Akinyanju, 1976 *Ann Clin Lab Sci.*, 6(6):521-4; Westerman et al., 1964 *Blood*, 2:3, Nayak et al. 2008, *Vascular Health and Risk Management*, 4(4) 893-899.

In another embodiment, subjects according to the invention are subjects suffering from decreased plasma levels of lipophilic antioxidant (Ama Moor et al., 2016, *BMC Clinical Pathology*, 16:15-20, Hermann et al, 2016, *J Pediatr (Rio J) in press.*, Alassane et al., 2014, *African Journal of Biochemistry Research*, 8(2), 39-42; Natta et al. 1988, *Eur J Haematol*, 41:131-135, Voskou et al., 2015 supra).

In another embodiment, subjects according to the invention are subjects suffering from microvascular complications due to pathological red blood cell functions hemorheological abnormalities associated with high red blood cell membrane cholesterol and low plasma HDL antioxidant level.

In another embodiment, subjects according to the invention are subjects suffering from sickle cell disease.

In another particular embodiment, subjects according to the invention are subjects suffering from sickle cell disease, wherein subjects are characterised by presence of methylenetetrahydrofolate reductase (MTHFR) polymorphisms, such as a single point mutation in MTHFR gene, for example 677C>T (MTHFR 677T mutation). Patients with MTHFR 677T mutation are characterized by a depletion of antioxidant capacity, according to the decreased catalase activity, and a reduction of about 30% of glutathione levels (da Silva et al., 2017, *Free Radic Biol Med.*, 106: 53-61).

In another embodiment, subjects according to the invention are subjects suffering from Thalassemia.

In another embodiment, subjects according to the invention are subjects suffering from diabetes.

Use of Combinations of the Invention

According to another aspect, the invention provides an agent increasing HDL activity for use in the prevention and/or treatment of a disease or disorder characterized by acute and chronic complications associated with red blood cell dysfunction, increased red blood cell cholesterol and decreased plasma levels of lipophilic antioxidant, in particular for the prevention and/or treatment of acute and chronic complications associated with red blood cell dysfunction in sickle cell disease, thalassemia and diabetes, wherein said agent is to be administered in combination with at least one liposoluble antioxidant or a mixture thereof.

According to a further aspect, the invention provides a combination according to the invention wherein at least one of said agent (increasing HDL activity or liposoluble antioxidant or a mixture thereof) of said combination is to be administered orally.

According to a further aspect, the invention provides a combination according to the invention wherein at least one of said agent (increasing HDL activity or liposoluble antioxidant or a mixture thereof) of said combination is to be administered by injection.

According to a further aspect, the invention provides a combination according to the invention wherein said combination is to be administered orally.

According to a further aspect, the invention provides a combination according to the invention wherein said combination is to be administered by injection, in particular by parenteral, subcutaneous or intravenous administration.

According to another aspect, the invention provides a method of preventing and/or treating acute and chronic complications associated with red blood cell dysfunction in sickle cell disease, thalassemia and diabetes, said method comprising administering at least one compound increasing HDL activity in combination with at least one liposoluble antioxidant or a mixture thereof to a subject in need thereof.

The invention encompasses the administration of an agent increasing HDL activity according to the invention or of a pharmaceutical formulation thereof, wherein an agent increasing HDL activity or the pharmaceutical formulation thereof is administered to an individual prior to, simultaneously or sequentially with at least one liposoluble antioxidant or a mixture thereof, in an effective amount. Agents increasing HDL activity or the pharmaceutical formulations thereof that are administered simultaneously with said at least one liposoluble antioxidant or mixtures thereof, can be administered in the same or different composition(s) and by the same or different route(s) of administration.

According to another aspect, the invention provides a method or a use according to the invention, wherein a pharmaceutical composition according to the invention is to be administered.

According to one aspect, a combination of the invention advantageously prevents or decreases or treats the microvascular complications of sickle cell disease and thalassemia and restores red blood functions.

According to a further aspect, a combination of the invention advantageously normalizes red blood cell membrane cholesterol concentration and decreases oxidative stress both parameters being pathologically affected in SCD, thalassemia and diabetes secondary to low levels of plasma HDL and decreased absorption of dietary lipophilic antioxidant.

EXAMPLES

The following abbreviations refer respectively to the definitions below:

Apo (Apolipoprotein); HDL (High Density Lipoprotein), LCAT (Lecithin Cholesterol Acyl Transferase); LDL (Low Density Lipoprotein; LXR (Liver X Receptor), RBC (red blood cell); ROS (reactive oxygen species).

Example 1: Administration of a Combination of Human Recombinant LCAT and Lutein-Zeaxanthin Mixture A combination of the invention comprising human recombinant LCAT as an agent increasing HDL activity and a combination of lutein-zeaxanthin were used in the treatment of SCD using a mouse SCD model (Fabry, 1993, *Cell Mol Life Sci.*, 49:28-36).

Human recombinant LCAT rhLCAT (ACP-501) (US 2014/0023631 is infused intravenously over 1 hour on 3 occasions in a dose optimization phase (0.3, 3.0, and 9.0 mg/kg), then 3.0 or 9.0 mg/kg every 1 to 2 weeks for 7 months in a maintenance phase, with the daily oral administration of 5, 10, 20 mg lutein-zeaxanthin such as Floraglo® (Kemin industries, USA) described in U.S. Pat. No. 6,663,900. Various parameters such as increased plasma LCAT activity, HDL particle number, HDL cholesterol, ApoA1, plasma liposoluble antioxidant levels and decreased in oxidative stress markers (such as MDA, lipid peroxydes, conjugated dienes) are measured. Tissue and cellular liposoluble antioxidant levels are also measured, especially in RBC. RBC count and hematocrite together with RBC rheological properties are monitored.

Example 2: Administration of a Combination of ApoA1 or ApoA1 Mimetics and Lutein-Zeaxanthin Mixture A combination of the invention comprising at least one ApoA1 mimetic (including ApoA1-mimetic peptides) such as D-4F and/or full-length ApoA1 prepared as described in U.S. Pat. No. 9,187,551 or 8,436,152 as an agent increasing HDL activity and a combination of lutein-zeaxanthin were used in the treatment of SCD Ryan et al., 1997, Science, 278, 5339, 873-876. ApoA1 mimetics and/or full-length ApoA1 adequately formulated (U.S. Pat. Nos. 9,125,943, 8,999,920, 9,439,946, 6,287,590 and 9,187,551) are administered subcutaneously, intravenously or orally at therapeutic efficacious doses with the simultaneous daily oral administration of 5 or 10 or 20 mg lutein-zeaxanthin such as Floraglo® (Kemin industries, USA). Read-out as described in Example 1 are monitored.

Example 3: Administration of a Combination of Apolipoproteins or Mimetic Peptides Thereof and Lutein-Zeaxanthin Mixture A combination of the invention comprising at least one Apolipoprotein selected from ApoA1, ApoA2, ApoE, ApoC1, ApoC3, ApoL, ApoM, ApoJ, ApoAIV or at least one alpha helix mimetic peptides thereof prepared as described in U.S. Pat. Nos. 9,125,943, 8,999,920, 9,439,946, 6,287,590 or U.S. Pat. No. 9,187,551 as an agent increasing HDL activity and a combination of lutein-zeaxanthin were used in the treatment of SCD validated using an SCD mouse model such as described by Ryan et al. 1997, *Science*, 278, 5339, 873-876. ApoA1, ApoA2, ApoE, ApoC1, ApoC3, ApoL, ApoM, ApoJ, ApoAIV protein or peptide adequately formulated are administered subcutaneously, intravenously or orally at therapeutic efficacious doses with the simultaneous daily oral administration of 5 or 10 or 20 mg lutein-zeaxanthin such as Floraglo® (Kemin industries, USA). Read-out as described in Example 1 are monitored.

Example 4: Administration of a Combination of Fenofibrate and a Lutein-Zeaxanthin Mixture Patients are treated daily with a therapeutically active oral dose of micronized fenofibrate (for example 150 mg per day) as an agent increasing HDL activity with the simultaneous daily oral administration of 5 or 10 or 20 mg lutein-zeaxanthin such as lutein-zeaxanthin such as Floraglo® (Kemin industries, USA). Read-out as described in Example 1 are monitored.

Example 5: Administration of a Combination of a LXR Agonist and Lutein-Zeaxanthin Mixture Patients are treated daily with a therapeutically active oral dose of a LXR agonist such as described in U.S. Pat. No. 7,579,504, as an agent increasing HDL activity with the simultaneous daily oral administration of 5 or 10 or 20 mg lutein-zeaxanthin such as lutein-zeaxanthin such as Floraglo® (Kemin industries, USA). Read-out as described in Example 1 are monitored.

Example 6: Administration of a Combination of Oral CETP Modulators/Inhibitors and Lutein-Zeaxanthin Mixture Patients are treated daily with a therapeutically active oral doses of a CETP modulator/inhibitor for example 150, 300, 450 or 600 mg of dalcetrapib as an agent increasing HDL activity with the simultaneous daily oral administration of 5 or 10 or 20 mg lutein-zeaxanthin such as Floraglo® (Kemin industries, USA). Read-out as described in Example 1 are monitored.

Example 7: Resistance to Cholesterol Depletion of RBC from SCD Patients

Blood was collected from four healthy control subjects using citrate as anticoagulant. After low speed centrifugation, the RBC pellet was washed with isotonic phosphate buffered saline (PBS) and re-suspended in PBS (hematocrit 20%).
To confirm the difference in membrane cholesterol in RBC from SCD compared to healthy subjects, RBC's sensitivity to the cholesterol depleting agent methyl-beta-cyclodextrine was assessed. RBCs were incubated for 20 min at 37° C. in the presence of 2.5 mM or 10 mM methyl-beta-cyclodextrine (Sigma ref. C4555-5G) as described by Motayama et al., 2009, *Biol. Pharm. Bull.*, 32(4) 700-705. RBC membrane deformability was assessed by ektacytometry (Mechatronics) as described by Renoux et al., 2016, *Clin Hemorheol Microcirc.*, 62(2):173-9 at shear rate of 3 Pa and 30 Pa.

It was confirmed that 10 mM methyl-beta-cyclodextrine produced a marked hemolysis and significant decrease of RBC deformability only in RBC from healthy control while RBC from 4 SCD subjects appeared to be resistant to the cholesterol depleting effect of 10 mM methyl-beta-cyclodextrine and resulting hemolysis. This supports not only the hypothesis of a higher cholesterol content of the membranes of RBC from SCD patients but also that the use of a cholesterol depleting agent alone is not able to diminish the complications of SCD due to RBC dysfunctions.

Example 8: Effect of a Combination of HDL and Lutein on RBC

The RBC were prepared as described in Example 7 and the effect of HDL with or without lutein on the oxidative stress status of RBC was determined using RBC from healthy subjects incubated for 20 min in presence of 100 µM HDL isolated from human plasma (Sigma ref L-1567) in presence or absence of 1 µM or 10 µM lutein (Bertin pharma ref. 1001081). Reactive oxygen species (ROS) were measured as Median Fluorescence Intensity (MFI) by flow cytometry similarly to Amer et al., 2003, *Eur J Haematol*, 70(2):84-90. Whereas HDL decreased ROS by 7.4% and 1 µM lutein decreased ROS by 9.2%, the combination of HDL with 1 µM lutein led to a decrease in ROS of 22.6% suggesting a synergic effect of their combination (Table 1) on RBCs.

TABLE 1

| | mean MFI | SEM | % control |
|---|---|---|---|
| Control | 42.2 | 11.6 | |
| HDL 100 µM | 39.0 | 12.4 | −7.4 |
| Lutein 1 µM | 38.3 | 7.5 | −9.2 |
| Lutein 10 µM | 26.8 | 8.0 | −36.4 |
| HDL 100 µM + Lutein 1 µM | 32.6 | 9.6 | −22.6 |

These data suggest that such a combination would be beneficial to SCD patients since they suffer from an accelerated oxidative damage status in RBC.

The invention claimed is:
1. A method of treating sickle cell disease, diabetic red blood cell dysfunction, or thalassemia comprising administering at least one agent increasing High Density Lipoprotein (HDL) activity in combination with at least one liposoluble antioxidant selected from a xanthophyll, lutein, zeaxanthin, meso-zeaxanthin, astaxanthin, beta-cryptoxanthin, a tocopherol isomer or derivative thereof selected from alpha-, beta-, gamma- and delta-tocopherol and a tocotrienol isomer or derivative thereof selected from alpha-, beta-, gamma- and delta-tocotrienol or a mixture of said at least one agent increasing HDL activity and said at least one antioxidant to a subject having sickle cell disease, diabetic red blood cell dysfunction, or thalassemia, wherein said at least one agent increasing HDL activity is a Cholesteryl Ester Transfer Protein (CETP) modulator selected from dalcetrapib and anacetrapib and said at least one agent increasing HDL activity and said at least one liposoluble antioxidant are administered without additional active agents.

2. The method according to claim 1, wherein said subject has sickle cell disease.

3. The method according to claim 1, wherein said subject has a diabetic red blood cell dysfunction.

4. The method according to claim 1, wherein said CETP modulator is dalcetrapib.

5. The method according to claim 1, wherein said at least one liposoluble antioxidant is selected from a xanthophyll, a tocopherol isomer or derivative and a tocotrienol isomer or derivative thereof.

6. The method according to claim 1, wherein said combination is administered orally.

7. The method according to claim 1, wherein said CETP modulator is anacetrapib.

8. The method according to claim 1, wherein said method comprises administering lutein and dalcetrapib or anacetrapib to said subject having sickle cell disease.

9. The method according to claim 1, wherein said subject has thalassemia.

10. The method according to claim 1, wherein said method comprises administering lutein and dalcetrapib or anacetrapib to said subject having thalassemia.

11. The method according to claim 8, wherein said method comprises administering lutein and dalcetrapib to said subject having sickle cell disease.

12. The method according to claim 8, wherein said method comprises administering lutein and anacetrapib to said subject having sickle cell disease.

13. The method according to claim 10, wherein said method comprises administering lutein and dalcetrapib to said subject having thalassemia.

14. The method according to claim 10, wherein said method comprises administering lutein and anacetrapib to said subject having thalassemia.

* * * * *